United States Patent
Lee et al.

(10) Patent No.: US 9,901,923 B2
(45) Date of Patent: Feb. 27, 2018

(54) MOBILE MOLECULAR DIAGNOSTICS SYSTEM WITH WIRELESS COMMUNICATION

(71) Applicant: THE REGENTS OF THE UNIVERSITY OF CALIFORNIA, Oakland, CA (US)

(72) Inventors: Luke P. Lee, Orinda, CA (US); Jun Ho Son, Richmond, CA (US); Sang Hun Lee, Albany, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/345,148

(22) Filed: Nov. 7, 2016

(65) Prior Publication Data

US 2017/0297020 A1      Oct. 19, 2017

Related U.S. Application Data

(60) Provisional application No. 62/252,288, filed on Nov. 6, 2015.

(51) Int. Cl.
*A61B 5/145* (2006.01)
*A61B 5/15* (2006.01)
(Continued)

(52) U.S. Cl.
CPC ...... *B01L 3/502715* (2013.01); *A61B 5/1459* (2013.01); *A61B 5/1491* (2013.01);
(Continued)

(58) Field of Classification Search
None
See application file for complete search history.

(56) References Cited

U.S. PATENT DOCUMENTS

| 2005/0105077 A1* | 5/2005 | Padmanabhan .... G01N 15/1484 356/39 |
| 2010/0173394 A1* | 7/2010 | Colston, Jr. ........... B01F 3/0807 435/287.2 |

OTHER PUBLICATIONS

Kim, B.N., Diaz, J.A., Hong, S.G., Lee, S.H., Lee, L.P., "Darkfield Smartphone Microscope With Nanoscale Resolution for Molecular Diagnostics", Proceedings of the 18th International Conference on Miniaturized Systems for Chemistry and Life Sciences (MicroTAS 2014), Oct. 26-30, 2014, San Antonio, Texas, USA, pp. 2247-2249.

* cited by examiner

*Primary Examiner* — Jennifer Wecker
(74) *Attorney, Agent, or Firm* — O'Banion & Ritchey LLP; John P. O'Banion

(57) ABSTRACT

A mobile, self contained molecular diagnostics system is provided with a microfluidic chip, detection apparatus and an integrated or wireless control interface and imager. The system provides automated sample preparation and rapid optical detection of multianalyte nucleic acids and proteins. On chip PCR may be performed to improve the optical fluorescence signal for nucleic acid detections. Plasmonic protein detection is performed using a dark field smartphone microscope. Dark field illumination is based on an evanescent field generated by LED total internal reflection. The smartphone element may also be used as an interface to control the detection apparatus, acquire images, process data and for wireless communications with remote computers. The handheld automated system has low power requirements and is particularly suited for point of care and on demand diagnostics in resource limited settings.

20 Claims, 6 Drawing Sheets

(51) Int. Cl.

| | | |
|---|---|---|
| *A61B 5/157* | (2006.01) | |
| *B01L 7/00* | (2006.01) | |
| *G01N 21/64* | (2006.01) | |
| *G01N 33/49* | (2006.01) | |
| *B01L 3/00* | (2006.01) | |
| *G01N 21/552* | (2014.01) | |
| *G01N 35/00* | (2006.01) | |
| *A61B 5/1459* | (2006.01) | |
| *A61B 5/1491* | (2006.01) | |
| *H04B 1/40* | (2015.01) | |

(52) U.S. Cl.
CPC .......... *A61B 5/14546* (2013.01); *A61B 5/157* (2013.01); *A61B 5/150099* (2013.01); *A61B 5/150251* (2013.01); *A61B 5/150755* (2013.01); *A61B 5/150824* (2013.01); *A61B 5/150854* (2013.01); *A61B 5/150984* (2013.01); *B01L 3/50273* (2013.01); *B01L 3/502753* (2013.01); *B01L 7/52* (2013.01); *G01N 21/554* (2013.01); *G01N 21/6458* (2013.01); *G01N 33/491* (2013.01); *G01N 35/00871* (2013.01); *A61B 2560/0209* (2013.01); *A61B 2562/0285* (2013.01); *B01L 2200/10* (2013.01); *B01L 2300/02* (2013.01); *B01L 2300/0654* (2013.01); *B01L 2300/0672* (2013.01); *B01L 2300/0681* (2013.01); *B01L 2300/0803* (2013.01); *B01L 2300/0816* (2013.01); *B01L 2300/0864* (2013.01); *B01L 2300/0896* (2013.01); *B01L 2300/18* (2013.01); *B01L 2400/049* (2013.01); *G01N 2035/00237* (2013.01); *G01N 2035/00366* (2013.01); *G01N 2035/00881* (2013.01); *G01N 2201/062* (2013.01); *H04B 1/40* (2013.01)

US 9,901,923 B2

MOBILE MOLECULAR DIAGNOSTICS SYSTEM WITH WIRELESS COMMUNICATION

CROSS-REFERENCE TO RELATED APPLICATIONS

This application claims priority to, and the benefit of, U.S. provisional patent application Ser. No. 62/252,288 filed on Nov. 6, 2015, incorporated herein by reference in its entirety.

STATEMENT REGARDING FEDERALLY SPONSORED RESEARCH OR DEVELOPMENT

This invention was made with Government support under HR0011-12-2-0003, awarded by The Defense Advanced Research Projects Agency. The Government has certain rights in the invention.

INCORPORATION-BY-REFERENCE OF COMPUTER PROGRAM APPENDIX

Not Applicable

BACKGROUND

1. Technical Field

The technology of this disclosure pertains generally to diagnostic devices and methods, and more particularly to a medical diagnostic microfluidic chip and detection apparatus that is self-contained, portable, inexpensive and capable of protein and nucleic acid detections.

2. Background Discussion

Point-of-care (POC) diagnostics allows a health care provider to diagnose in the physician's office, an ambulance, the home, the field, or in the hospital for timely, rapid treatment. Empowering clinicians to make decisions at the "point-of-care" has the potential to significantly impact health care delivery. The success of a potential shift from curative medicine, to predictive, personalized, and preemptive medicine could rely on the development of portable diagnostics systems and monitoring devices for POC testing.

Ideal point-of-care medical diagnostic assays should be low in cost, portable, simple, rapid, and capable of on chip protein detections and quantitative nucleic acid detection. However, most systems that have been developed to date have not been truly autonomous. Most diagnostic assays that are commercially available provide only positive/negative readouts, or require additional separate steps for protein or DNA detections. The current standard for quantitative testing is real-time PCR that is a process that is not well suited for low-cost field operations. This method generally involves laboratory equipment (e.g. thermal-cyclers and centrifuges) that require external power sources, several hours of assay time, multiple manual sample preparation steps, and trained technicians. The polymerase chain reaction processes has become an essential technique in clinical laboratories, agricultural science, environmental science, and forensic science.

The need for portable, inexpensive, and self-contained lab-on-a-chip diagnostic devices is particularly acute in lesser developed countries with limited infrastructure and medical resources as well as in remote locations and field operations. These locations typically limited laboratory facilities, limited supplies and limited power availability.

Therefore there is a need for automatic, self-contained devices with low power requirements that can produce fast and reliable results that greatly reduces the risk of human error. There is also a need for integrated devices that encompass sample collection, sample preparation, analyte-specific reactions, signal production and detection and the reporting of a patient specific result. The present technology satisfies these needs and is generally an improvement in the art.

BRIEF SUMMARY

The technology described herein provides an apparatus and methods for producing a point-of-care diagnostic microfluidic chip design and detector system that is portable, low cost and capable of protein and nucleic acid detections. Generally, the microfluidic chip and detection platform are designed to function in low resource settings such as in rural villages in third world countries where there may be a lack of infrastructure, centralized labs, electricity, medical personnel, and funds for costly equipment.

The mobile molecular diagnostics system leverages efficient and dependable blood sampling, automated sample preparation, rapid optical detection of multi-analyte nucleic acids and proteins, and user-friendly systems integration with wireless communication. The preferred apparatus provides a hand-held automated system with an adaptive sample control module, an optical signal transduction module, and an interface to a smartphone to make the system a reliable and field-applicable system for point-of-care and on-demand diagnostics.

The preferred chip design has a closed microfluidic system with an integrated sample pad with hollow microneedles for single step blood acquisition directly to the chip. The chip may have a membrane filter as part of the microfluidic system for blood sample separations. The chip may optionally have a dilution buffer intake for additional buffer to fill the device and to mix buffer with the blood sample for processing.

The microfluidic system can be designed with microstructures, such microwells and microchannels that can be used to perform specific separation and detection functions. The microstructures of the chip are designed and configured with dimensions and reagents to perform plasmonic protein detection and on chip PCR for nucleic acid detection functions.

The distal end of the chip is designed to fit within a slot of the detection apparatus and engage a socket within the slot. Electrical contacts and fluidic ports on the chip engage corresponding contacts and ports of the apparatus that are connected to a vacuum pump and associated vacuum system or electrical power that are controlled by a controller for autonomous operation.

The slot that receives the microfluidic chip within the detection apparatus portion of the system may also have controlled illumination sources such as light emitting diodes and waveguides to direct light to portions of the chip. The detection apparatus also has a power source, optional heating elements, waste receptacles and chip imaging and computation functions used in connection with protein and nucleic acid detections.

In one embodiment, the image capture and data processing is performed by a separate computing device such as a smartphone, tablet or similar device. The device may also be an interface with the system controller. In the preferred embodiment, the smartphone is converted to a dark-field microscope by an attachment that provides dark-field illumination and an external lens for magnification.

The dark-field illumination and plasmonic protein detection scheme of the apparatus takes advantage of the evanescent field generated by LED total internal reflection (TIR) in the waveguide and chip substrate. The field energy of a guided wave can extend outside of the waveguide boundaries, and this field is known as the evanescent field. An evanescent field is created anytime that light undergoes total internal reflection. The penetration of the evanescent field outside of the boundaries will depend upon the wavelength of the light, the refractive index ratio of the waveguide to the surroundings and the intensity of the photons. Generally, the evanescent field energy will decay exponentially with distance from the boundary surface.

In this embodiment, white LED's are used for nanoparticle excitation of nanoparticles bound to a nanodisc. The scattered light at the surface of nanoparticle is collected without any background due to the short penetration depth of the evanescent field.

For nucleic acid detection, blue LED's may be used for fluorescent excitation. The fluorescence intensity is then imaged and analyzed by the smartphone PCR and may be performed prior to imaging to improve the signal. Thermocyling with a micro-heater or other techniques may be used to assist the amplification in one embodiment. A thin film photothermal heater within the wells for the nucleic acid amplification using photonic PCR is preferred.

It will be appreciated that the technology provides for point-of-care testing for human, animal healthcare, forensic science and food, environmental monitoring. The technology can be used to obtain simultaneous detection of protein and nucleic acids for point-of-care diagnostics with low cost, simple operation, and low power consumption. Further, the technology is generally well-suited as a molecular diagnostics system for point-of-care testing.

According to one aspect of the technology, a microfluidic chip is provided with an integrated design for a self-contained and fully-automated test with easily interpreted results that requires no specialized training so that any user can operate the apparatus without technical training.

Another aspect of the technology is to provide a microfluidic chip that is ideal for optical detection and quantification.

Another aspect of the technology is to provide an apparatus and method for on chip quantitative digital nucleic acid detection and specific protein detection directly from human blood with microwell compartmentalization and automatic blood cell acquisition, separation and analysis.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 1 is a schematic perspective view of a mobile molecular diagnostic sensing system for Point-of-Care (POC) diagnostics. The system has a chip with a microfluidic system with an integrated molecular diagnostic device for the simultaneous detection of protein and nucleic acids with contactless optical excitation and readout systems. The user interface has been removed for clarity.

FIG. 5A is a schematic perspective view of the system showing insertion of the selected chip into the detection apparatus.

FIG. 5B is a schematic perspective view of the chip seated into the socket of the detection apparatus.

FIG. 5C is a schematic perspective view of the placement of the finger of the subject on a sampling pad of hollow microneedles that needles penetrate the epidermal layer of skin to sample blood.

FIG. 5D is a schematic perspective view of the chip with a dilution buffer drop to fill the microfluidic system elements with the sample.

Figure 6A:
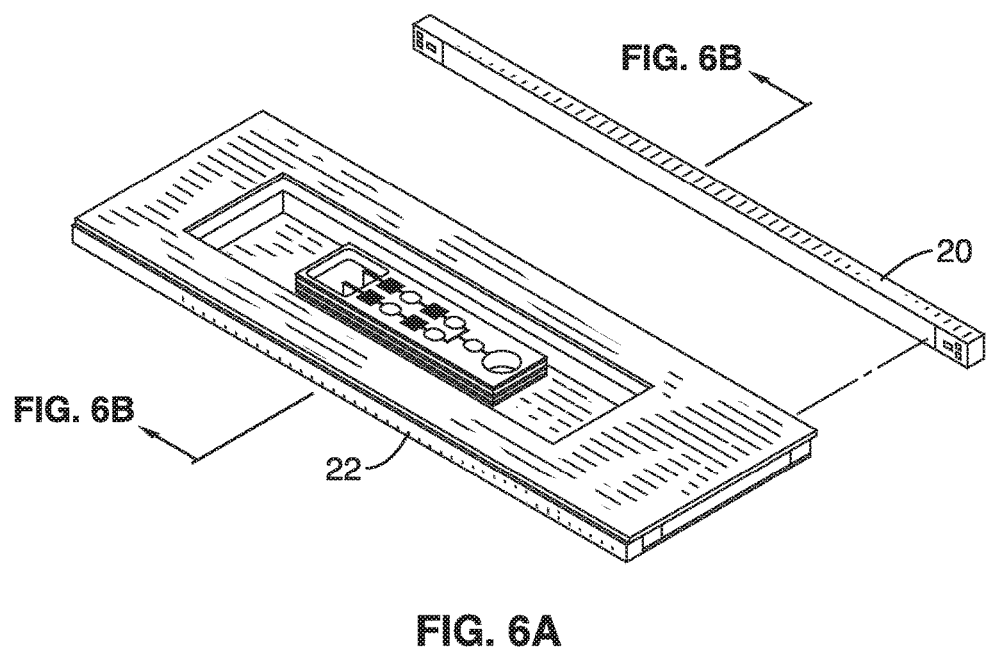
FIG. 6A is a perspective view of the optical detection module of the detection apparatus.
Figure 6B:
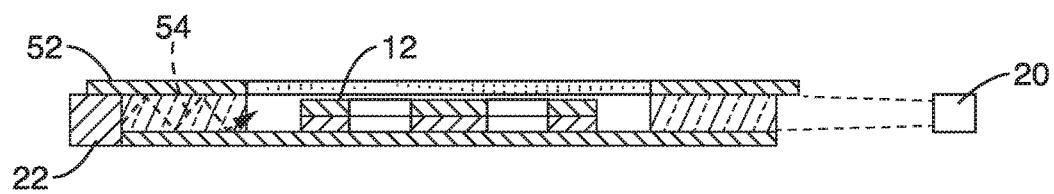

FIG. 6B is a cross-sectional view of the optical detection module for the plasmonic protein detection and fluorescent nucleic acids detection. White and blue LEDs are used for the plasmonic protein and fluorescent nucleic acids detection, respectively. A simple plastic wave guide is used for the excitation of gold nanoparticles (GNPs).

DETAILED DESCRIPTION

Referring more specifically to the drawings, for illustrative purposes, embodiments of systems, apparatus and methods for plasmonic protein detection and nucleic acid detection from a sample are generally shown. Several embodiments of the technology are described generally in FIG. 1 through FIG. 6B to illustrate the diagnostic systems, apparatus and methods. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

The apparatus and methods are illustrated in a diagnostic system 10 with a multi-welled microfluidic chip 12 and detection apparatus 14 as shown in the expanded view of FIG. 1 and FIG. 5A through FIG. 5C. Generally, the molecular diagnostics system 10 shown in FIG. 1 has a diagnostic detection apparatus 14 with electronic readout and control functions that has a socket 26 that is configured to receive and control the actions of chip 12.

Figure 1:
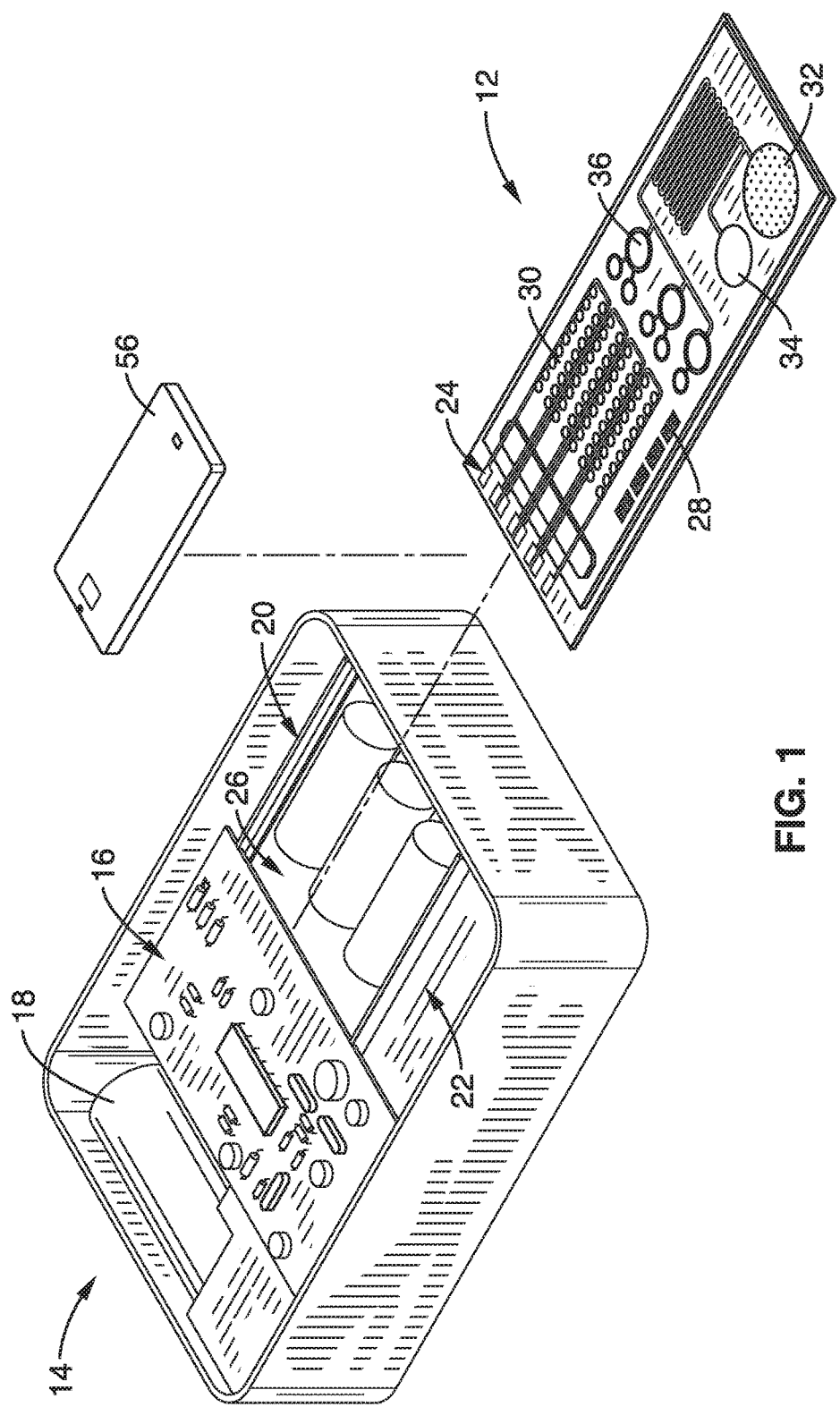

The base detection apparatus 14 embodiment illustrated in FIG. 1 has a control module 16 that preferably has an interface to allow control over the detection activities of the apparatus 14 and chip 12. The detection apparatus 14 shown in FIG. 1 has a vacuum assisted pump 18 for sample collection, microfluidic movements and diagnostic functions. The vacuum pump 18 also allows the possible reliable collection of a single large volume of blood, for example, obtained from the sample collection pad 32 that includes a number of microneedles to acquire a blood sample directly from a patient. In the embodiment shown, the vacuum pump 18 is powered by a conventional battery pack. However, in other embodiments, the pump 18 and control and display modules are powered by a plug and electrical outlet.

The control module 16 may have a programmable controller such as a computer controller with software as well as a microelectronic interface for autonomous operation. In the embodiment shown in FIG. 1, control operations are directed through wireless transmission to a smart telephone display interface. The camera, display, interface, processing and communications functions of the smartphone 56 may all be utilized by the control module 16.

Figure 2:
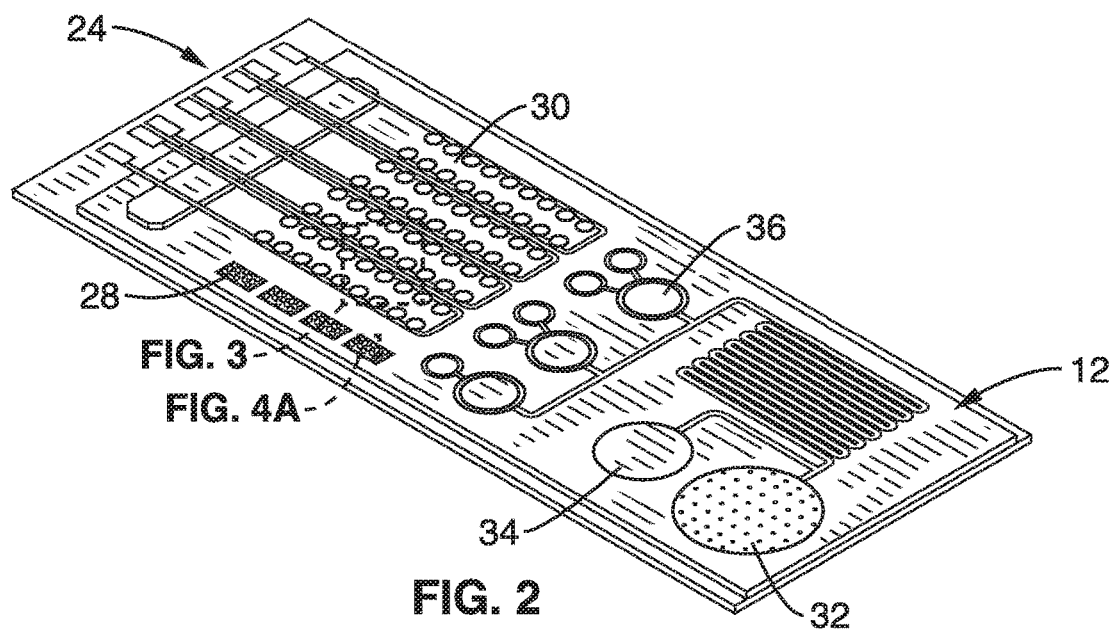
FIG. 2 is a schematic perspective view of a self-contained microfluidic chip with microneedle sample intake pad, membrane filter for blood separation, on-chip PCR for nucleic acid detections and plasmonic protein detection according to one embodiment of the technology.
Figure 3:
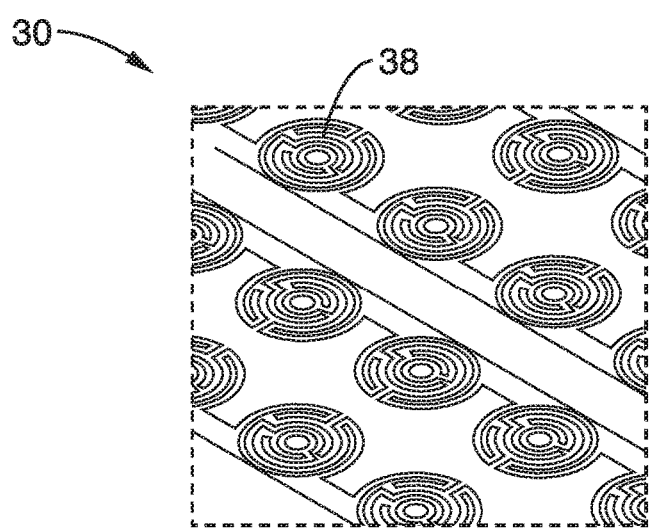
FIG. 3 is a detailed view of the wells of FIG. 2 for nucleic acid detection.

The chip 12 in this illustration has a simple construction and can be used for rapid and sensitive detection of nucleic acids and proteins with contactless optical excitation and readout systems. Referring also to FIG. 2 to FIG. 4, the design of chip 12 is configured for plasmonic ELISA and ultrafast plasmonic PCR.

The chip 12 preferably has an end that reversibly couples with socket 26 of the detection apparatus 14. The end of the chip 12 has a number of microfluidic and electronic attachment points 24 that align with corresponding points in the socket 26 of the apparatus receptacle that are controlled by the control module 16.

The end of the chip 12 is received by the detection apparatus in a rectangular receptacle defined by a distal socket with white LED's and waveguide 22 on one side for plasmonic detection and blue LED's and guide on the other for fluorescent detection. The linear guides 20 and 22 and chip 12 are sized to fit together to provide the proper illumination by the LED's and waveguides.

In the embodiment shown in FIG. 2, the chip 12 has a sample inlet in the form of a pad of vertical microneedles for receiving a sample of blood. The sample inlet 32 may also be a simple port or panel. A buffer inlet 34 is also present to provide a pool of buffer to the sample and microfluidic system and to keep air out of the microchannels from the inlet 32. An optional membrane filter 36 that is capable of blood cell separations is provided in the combined sample and buffer lines of the chip 12.

The microfluidic system of chip 12 is connected to a selected detection scheme. In the design of the embodiment of FIG. 2, the chip 12 has a nucleic acid detection scheme 30 using ultrafast plasmonic PCR and a protein detection scheme 32 using plasmonic ELISA.

The nucleic acid detection scheme 30 uses a number of wells 38 for PCR or isothermal amplification and detection of nucleic acids as seen in the detail of FIG. 3. Normal PCR procedures require thermal cycling, or repeated temperature changes between two or three discrete temperatures to amplify specific nucleic acid target sequences. Resistive heating with microfabricated thin film heaters is most commonly used to control the chamber temperature in conventional microfluidic-based PCR systems. However, this method requires a complicated fabrication process to integrate the thin film heater and resistance temperature detection sensor on the chip.

Therefore, the nucleic acid detection module 30 of chip 12 is preferably configured to use an ultrafast photonic PCR method that combines the use of a thin Au film in the wells 38 as a light-to-heat converter and light-emitting diodes as a heat source. When the photons from the LED excitation source reach the surface of the thin Au film in a well 38, plasmon-assisted strong light absorption can occur. This light absorption excites electrons near the surface of the film to higher energy states generating hot electrons. These hot electrons can quickly reach a temperature of several thousand degrees Kelvin due to their small electronic heat capacity and rapidly diffuse throughout the thin Au film, creating a uniform distribution of hot electrons. Rapid heating is followed by cooling to equilibrium by energy exchange between the hot electrons and the lattice phonons.

Accordingly, when the thin Au films in the wells 38 are illuminated, a large temperature difference between the hot metal surface and the cooler surrounding solution occurs, resulting in the heating of the surrounding solution. Fast cooling of the heated solution can also be achieved by the heat dissipation through the thin Au film when a light source is turned off. This efficient photonic based heating procedure could be generally integrated into a variety of chip designs and procedures, including on-chip thermal lysis and heating for isothermal amplifications.

The embodiment of chip 12 shown in FIG. 1 and FIG. 2 also has the capability of protein detections such as by plasmonic enzyme linked immunosorbent immunoassay (ELISA) techniques for the ultrasensitive detection of protein markers by colormetric detection.

Figure 4A:
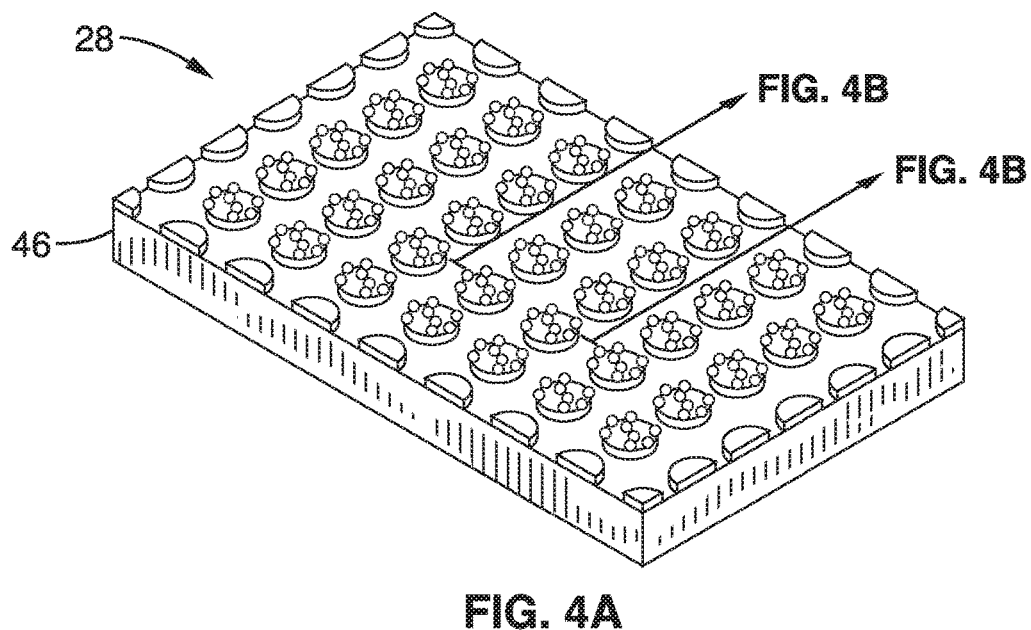
FIG. 4A is a perspective view of the plasmonic protein detection modules of the chip of FIG. 2.
Figure 4B:
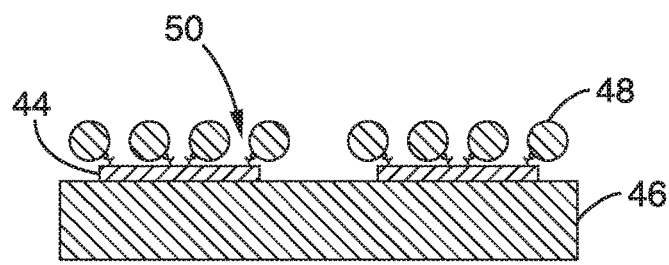
FIG. 4B is a cross-sectional view of the substrate, disks binding molecules and particles of the protein detection modules of FIG. 4A.

FIG. 4A depicts schematically a plasmonic protein detection module 28 on a nano-patterned substrate 46 that is configured for signal enhancement. For the further enhancement of plasmonic light scattering to improve the limit of detection, the nano-patterned substrate has a metal (Au) nano-disk 44 and at least one metal nanoparticles 48 can be used enhanced plasmon scattering as shown in the detailed view of FIG. 4B. Gold nanoparticles (GNP) 48 that are approximately 40 nm to 60 nm in diameter are preferably placed on an approximately 200 nm diameter gold nano-disk 44 within the detection structure 28 are preferred for electric field enhancement of the GNP and enhanced plasmon scattering are preferred.

The preferred assay format for the protein detection module 28 is based on the generation of colored solutions with characteristic tonality in the wells when in the presence of a specific analyte 50. This platform can be adapted to different microfluidic optical detection schemes that are centered on a change in optical characteristics with the binding of the target.

Operation of one embodiment of the mobile molecular diagnostics system with an end-to-end detection capability from blood sampling to data analysis is shown in FIG. 5A through FIG. 5D. In this illustration a smartphone can be used for the data image capture, data analysis, storage and wireless transmission. The system design shown in FIG. 5A to FIG. 5D is configured for resource limited settings such as in developing countries or in remote locations. The detection apparatus 14 is self contained and does not require an external power supply or pumps etc. and does not require any sophisticated instruments at a clinic to read the results beyond the smartphone.

The chip 12 that is selected is also self-contained and adapted for specific detections and sample types. Only the sample and dilution buffer are needed to operate the apparatus 14.

Figure 5A:
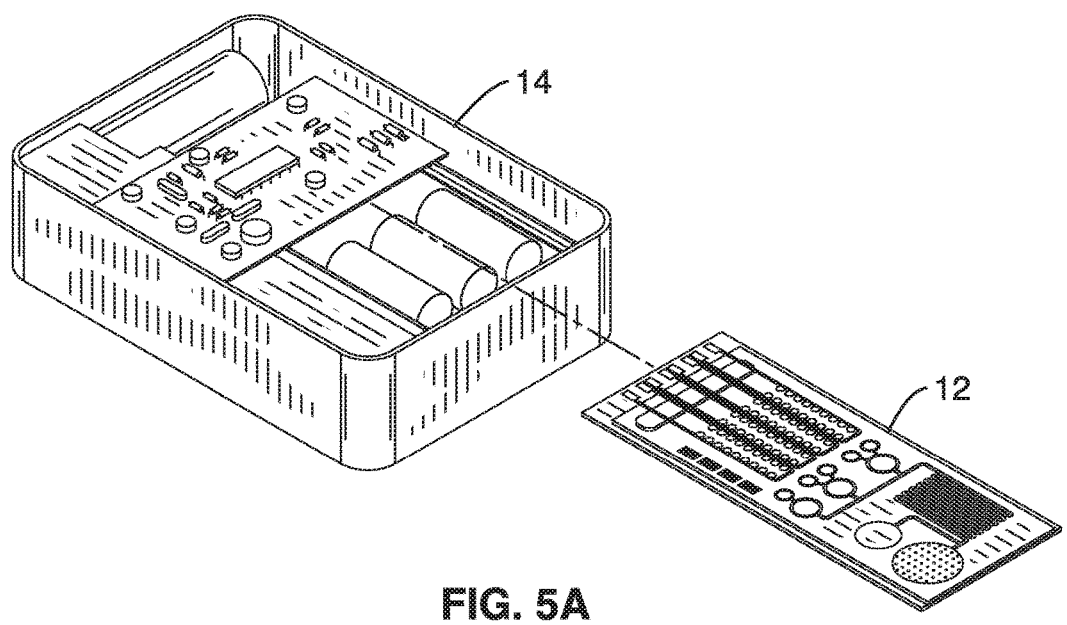
FIG. 5A to FIG. 5D illustrates system operation of the mobile molecular diagnostics system with an end-to-end detection capability from blood sampling to data analysis. A smartphone can be used for the data image capture, data analysis, storage and wireless transmission.
Figure 5B:
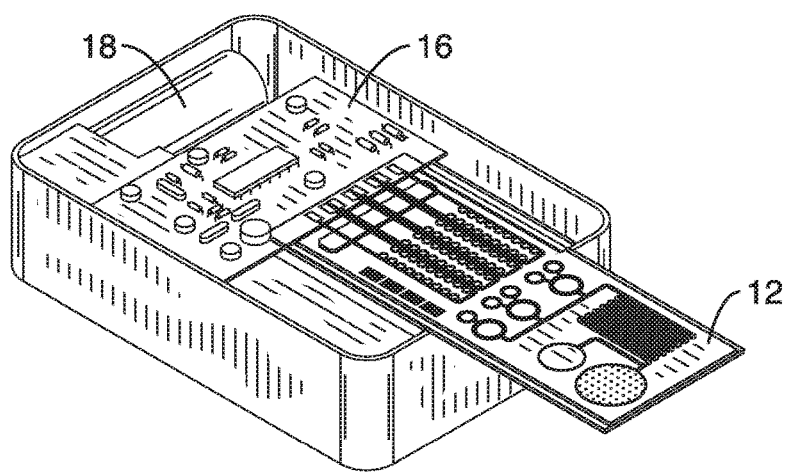

Once the desired sample type for analysis and the appropriate chip 12 type are selected, the selected chip 12 is inserted into the apparatus 14 as seen in FIG. 5B. The insertion end of the chip has microfluidic ports and electrical contacts that align with corresponding ports and electrical contacts in the socket 26 of the control 16 of the apparatus 14. The insertion of chip 12 also aligns the base of the chip with illumination sources such as a LED bar 20 or wave guide 22 as shown in FIG. 6. Light sources such as laser or LED may also be place beneath chip or be directed perpendicularly to the chip 12 to illuminate specific portions of the chip from below in some embodiments.

Figure 5C:
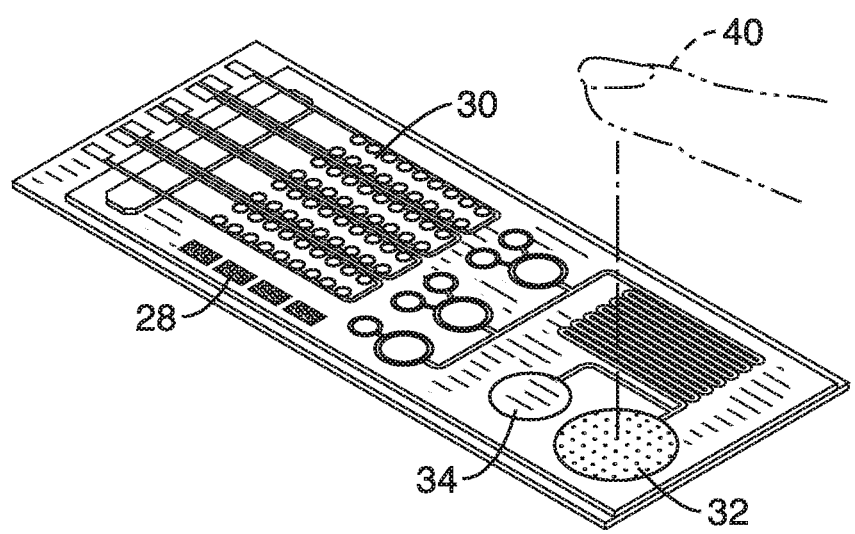

The subject then places a finger 40 on the pad 32 of hollow microneedles for extraction of a sample in this embodiment as shown in FIG. 5C. The apparatus 14 that is reversibly coupled to the chip 12 is not shown in FIG. 5C and FIG. 5D for clarity.

The end-to-end detection capability of the system 10 is achieved through integrated hollow microneedles 32 and the vacuum-assisted pump 18 of the detector apparatus 14. Specifically, once the user places a fingertip 40 on the chip 12 and presses the sampling pad 32 having hollow microneedles, the hollow microneedles on the pad 32 will penetrate the epidermal layer of skin of the finger 40 to sample blood from capillary vessels underneath. The vacuum-assisted pump 18 will then start generating a negative pressure to withdraw enough volume of blood into the device. When a necessary volume of blood is withdrawn (>100 µl), the user will take the finger 40 away from pad 32 and the system will run the necessary subsequent steps, i.e., sample preparation, sample delivery, and nucleic acids/proteins detection, as preprogrammed via a smartphone or a microcontroller.

Figure 5D:
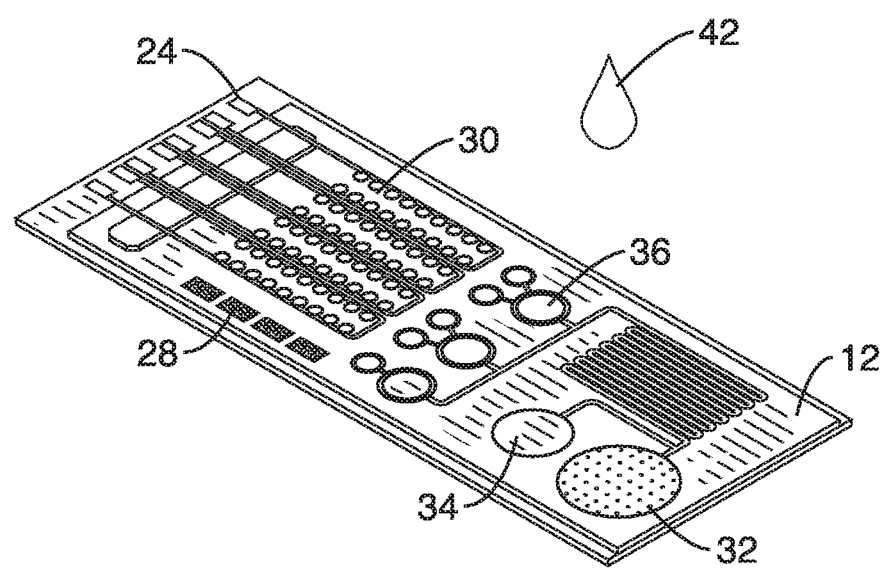

As shown in FIG. 5D, the chip 12 has a buffer port 34 that allows the introduction of a pool of dilution buffer 42 that will fill the microfluidic systems with blood and buffer for analysis.

Analysis of the sample in the inserted chip 12 is by plasmonic protein detection and fluorescent nucleic acids detection in the configuration illustrated in FIG. 6A. White and blue LEDs are used for the plasmonic protein and fluorescent nucleic acids detection, respectively. A simple plastic wave guide 22 is used for the excitation of gold nanoparticles (GNPs) or fluorescent particles as shown in FIG. 6B. As shown in the expanded view of FIG. 6A, the light source 20 is a bar of light emitting diodes of a suitable wavelength to cause fluorescent excitation of nucleic acids. The second light source is also a bar of white light emitting diodes 22 coupled to a wave guide 52 that produces evanescent field energy within one or more wells generated by LED total internal reflection 54 of the light source as seen in FIG. 6B.

In one embodiment, the optical detection of proteins is based on integrative Light Amplifications of Multiple Plasmonic probes (iLAMPs), which form a sandwich immunoassay architecture using gold nanoplasmonic protein probes and gold optical antenna array as a ground layer for the maximization of optical signal amplification due to the matching plasmonic resonance frequencies.

The ground layer of gold optical antenna array also builds the foundation of signal gains from fluorescent probes in nucleic acids detections regardless of polymerase chain reaction (PCR) amplification or isothermal amplification methods of DNA since the selective resonant frequency of plasmon-induced optical antenna array allows a user to tune with a simple LED excitation. On the top of gold optical antenna array, conjugate and reagents are pre-stored and lyophilized for one-step detection.

Both nucleic acid and protein detection schemes require optical components such as LED light sources for excitation, waveguides, photodiodes, and an adapter to a smartphone camera (or CMOS image sensors), which are either commercially available in a small form factor or readily manufactured at low cost. All of the optical components can be easily integrated into the electronic system and coupled with the detection device 14.

Once the sample is introduced into the nucleic acid detection module 30 and the protein detection module 28 of the chip 12, the analysis is performed. Generally, for protein detections, the white LED's are actuated for nanoparticle excitation and an image is captured by a smartphone camera or by an integrated CMOS image sensor connected to the controller 16. The illumination source is then turned off.

For nucleic acid detection, blue LED's are actuated for fluorescence excitation. In one embodiment, the nucleic acid analysis performs polymerase chain reaction or isothermal amplification directed by controller 16 before optical analysis. This includes thermocycling by a microheater or by plasmonic heating of nanodiscs directed by the controller 16.

Image capture by a smartphone camera or integrated sensors provides an image of fluorescence intensity that can then be analyzed. Analysis of the images can also be by smartphone acquisition and transmission to a central location for computer analysis by another system. The processed results can be sent back the smartphone.

The images of the optical colormetric signals and the fluorescence intensity etc. are preferably obtained with dark-field illumination and preferably with dark-field smartphone microscope. Dark-field illumination is based on evanescent field 42 generated by LED total internal reflection (TIR). The scattered light at the surface of the nanoparticles, for example, can be collected without any background due to the short penetration depth of evanescent field.

The display, imaging and data processing functions of the system can be integrated in the controller 16 of the detection apparatus 14 and the controller can have a processer and programming software to compute and display the results. However, in the preferred embodiment, the display, imaging and data processing functions are performed by a smartphone 56 in addition to control functions as shown in FIG. 1. In this embodiment, the controller 16 has a communications node that allows the controller 16 of the apparatus to have wireless communications with smartphone 56. The smartphone 56 has an interface and programming that wirelessly operates the control functions of the controller 16, such as pump control, heating element or light control for PCR and chip illumination control. In addition, the imaging and data processing functions of the system are also provided by the camera, storage, processer and programming of the smartphone 56 in this embodiment. The telephone, WiFi and Bluetooth capabilities of the smartphone 56 can also be utilized to communicate with remote computers that may perform the data processing and storage of the images acquired by the smartphone 56. The results processed by these remote computers can be transmitted back to the smartphone 56 as well as to other designated recipients.

The use of a smartphone 56 for the control interface, imaging and processing functions reduces the electrical energy demand and weight of the apparatus 14. This allows both the detection apparatus 14 and the imaging apparatus and processing of the smartphone 56 to be battery powered and eliminates the need for an outside power source.

Overall, the technology allows for simultaneous detections of protein and nucleic acids for point-of-care diagnostics with low cost, simple operation, and low power consumption. Additionally, the technology can obtain single molecule level detection limit of ELISA via LED-based total internal reflection excitation on the chip. Further, the technology provides an effective solution for interfacing molecular diagnostics with integrated information technology.

The technology described herein may be better understood with reference to the accompanying examples, which are intended for purposes of illustration only and should not be construed as in any sense limiting the scope of the technology described herein as defined in the claims appended hereto.

Example 1

In order to demonstrate the operational principles of the apparatus and synthesis methods, an apparatus was constructed having the features shown schematically in FIG. 1 with the integrated molecular diagnostic system for the simultaneous detection of protein and nucleic acids and mobile phone-based image acquisition and analysis.

Plasmonic protein detection was demonstrated using an Apple™ iPhone 4 and wave-guided excitation of gold nanoparticles by LED illumination. A sandwich immunoassay scheme was used for the detection of a specific protein and the secondary antibody was labeled with 40 nm gold nanoparticles. A low cost (~$4) iPhone microscope was used for higher magnification to capture images of plasmonic protein assay using iPhone 4. Images of the chip of captured proteins using the sandwich immunoassay were analyzed for quantitative analysis.

The improvement off the limits of detection through further enhancement of plasmonic light scattering with a nanodisk was also demonstrated. Initially, the light extinction spectra and enhancement of electric field for the 40 nm gold nanoparticle (GNP) with and without 200 nm gold (Au) nanodisk for plasmon scattering were calculated. A nanopatterned microfluidic substrate with a 40 nm gold nanoparticle and a 200 nm gold nanodisk was then prepared and tested. Plasmonic protein detection on the nano-patterned substrate for signal enhancement was then evaluated. Electric fields were found to be significantly enhanced with the use of the gold nanodisk compared to the GNP particle alone.

Optical fluorescent nucleic acid detection with the chip was also demonstrated. Changes of relative fluorescent intensity after polymerase chain reaction (PCR) with different copy numbers were observes and images were captured using an iPhone 4 camera and a conventional CMOS camera (Logitech webcam). It was shown that after PCR amplification, the smartphone camera 56 could successfully detect a variety of fluorescent signals.

Example 2

The functionality of the dark-field smartphone microscope and dark-field illumination based on the evanescent field generated by LED total internal reflection (TIR) were also demonstrated. The smartphone camera was converted to a dark-field microscope by an attachment that consisted of a dark-field illumination and external lens for magnification. An external lens (f=3 mm) was attached and aligned to the smartphone camera to magnify and capture scattering light from nanoparticles. The scattered light at the surface of the observed nanoparticles was collected without any background due to the short penetration depth of evanescent field.

Dark-field illumination methods were also compared. From a specimen slide populated with gold nanoparticles, SPR scattering images were taken after (a) oblique illumination and (b) LED TIR illumination.

Unlike oblique dark-field illumination that requires condenser and spider light stop, an evanescent field is used to avoid complexity of the system and to create highly localized illumination (fixed z) at the surface of specimen slide as shown in FIG. 4. It was observed that TIR illumination yields higher signal-to-noise ratio (SNR=Intensity/$\sigma_{noise}$) than that of oblique illumination, 19.3 and 12.5 respectively, for surface nanoparticle analysis. Thus, LED TIR is best for use for dark-field illumination in the smartphone attachment with its high SNR for sensitive imaging and compactness for portability.

With the LED illumination and an external lens, single nanoparticle resolution was conducted by imaging gold nanoparticles of various sizes using the single nanoparticle resolution of a dark-field smartphone microscope.

Smartphone images were initially obtained of 150-nm gold nanospheres on a specimen slide. Then single nanoparticles of 80-nm gold nanospheres, 100-nm gold nanospheres, and 150-nm gold nanoparticles were detected and imaged. The observed colors of each nanoparticle represent the surface plasmon resonance (SPR) wavelength of each particle.

A wide range of SPR wavelengths from gold nanorods (red), silver nanosphere (blue), and gold nanosphere (green) could be detected by smartphone RBG camera. Different SPR wavelengths for different sizes and types of nanoparticles were shown to be detectable with the use of a color image sensor of a smartphone.

Three microfluidic channels loaded with gold nanorods, silver nanospheres, and gold nanospheres were then illuminated using the same LED TIR. This resulted in a strong scattering of red, blue, and green for each of the respective particles. The capability to differentiate various plasmon-resonance wavelengths can potentially be useful to multiplex assays.

Example 3

The adaptability of the system to different optical detection schemes was further demonstrated by detecting a wavelength shift by gold nanoparticle aggregation. A bioassay of gold aggregation from biotin-streptavidin interaction was performed and imaged and analyzed with the dark-field smartphone microscope.

Gold nanoparticles with 80-nm diameters that are coated with biotin exhibit SPR wavelength with a green color. Gold nanoparticles that were 40 nm in diameter that were coated with streptavidin were also prepared and introduced to the first set of 80 nm particles. After introduction of the second particles, the gold nanoparticles start to aggregate due to the strong interaction of biotin-streptavidin. The SPR wavelength of observed particles shifted from green to orange in color indicating the aggregation of gold nanoparticles by biotin-streptavidin interaction.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit (CPU), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

From the description herein, it will be appreciated that that the present disclosure encompasses multiple embodiments which include, but are not limited to, the following:

1. A system for microfluidic sample analysis, the system comprising: (a) a microfluidic chip body comprising: (i) a plurality of enclosed wells; (ii) a sample inlet that receives a fluid sample; (iii) a network of microfluidic channels coupled to the wells with at least one inlet channel that transports a fluid sample from the sample inlet to one or more wells; and (iv) at least one vacuum port connected to the network of microfluidic channels, the vacuum port configured to be coupled to a vacuum source to draw fluid through the network of microfluidic channels and wells; (b) a detection assembly, the assembly comprising: (i) a housing with a slot opening configured to receive the microfluidic chip; (ii) a vacuum pump; (iii) a socket operably coupled to the vacuum pump, the socket configured to reversibly couple with at least one vacuum port of the microfluidic chip; (iv) one or more light sources directed to surfaces of the chip, the light sources configured for excitation of nanoparticles by illumination; (v) a controller coupled to the vacuum pump, light sources and a power supply; and (vi) an imager.

2. The system of any preceding embodiment, wherein the inlet of the microfluidic chip further comprises: a plurality of hollow micro-needles coupled to the channel; wherein a user places a fingertip on the plurality of hollow micro-needles, such that the one or more hollow micro-needles penetrates an epidermal layer of skin to sample blood from capillary vessels underneath; and wherein the vacuum pump generates a negative pressure within the inlet channel to withdraw a volume of blood into the microfluidic system.

3. The system of any preceding embodiment, the microfluidic chip further comprising: a membrane filter for blood separation coupled to the inlet channel and placed in the microfluidic network between the inlet and the wells.

4. The system of any preceding embodiment, the microfluidic chip further comprising: a buffer and reagent loading port connected to the inlet channel.

5. The system of any preceding embodiment, the wells of the microfluidic chip further comprising: a metal nanodisk within the wells for enhancement of plasmonic light scattering to improve the limit of detection.

6. The system of any preceding embodiment, the light source further comprising: a waveguide; and a plurality of light emitting diodes for wave guided excitation of nanoparticles by LED illumination.

7. The system of any preceding embodiment, the imager comprising: a smartphone microscope imaging dark-field illumination of the chip based on evanescent fields within one or more wells generated by LED total internal reflections of the light source.

8. The system of any preceding embodiment, the microfluidic chip further comprising: a second set of wells connected to the network of microfluidic channels; and microheating elements in proximity to the wells, the elements controlled by the controller.

9. The system of any preceding embodiment, the detection assembly further comprising: a second light source configured for fluorescent excitation of nucleic acids.

10. A system for microfluidic sample analysis, the system comprising: (a) a microfluidic chip body comprising: (i) a first and second set of a plurality of enclosed wells; (ii) a sample inlet that receives a fluid sample; (iii) a network of microfluidic channels coupled to the sets of wells with at least one inlet channel that transports a fluid sample from the sample inlet to the sets of wells; and (iv) at least one vacuum port connected to the network of microfluidic channels, the vacuum port configured to be coupled to a vacuum source to draw fluid through the network of microfluidic channels and wells; (b) a detection assembly, the assembly comprising: (i) a housing with a slot opening configured to receive the microfluidic chip; (ii) a vacuum pump; (iii) a socket operably coupled to the vacuum pump, the socket configured to reversibly couple with at least one vacuum port of the microfluidic chip; (iv) a first light source directed to surfaces of the chip, the light source configured for excitation of nanoparticles or fluorescent particles by illumination; (v) a second light source directed to surfaces of the chip, the second light source configured for fluorescent excitation of nucleic acids; (vi) a heating element; (vii) a controller coupled to the vacuum pump, light sources, heating element and a power supply; and (viii) an imager.

11. The system of any preceding embodiment, wherein the inlet of the microfluidic chip further comprises: a plurality of hollow micro-needles coupled to the channel; wherein a user places a fingertip on the plurality of hollow micro-needles, such that the one or more hollow micro-needles penetrates an epidermal layer of skin to sample blood from capillary vessels underneath; and wherein the vacuum pump generates a negative pressure within the inlet channel to withdraw a volume of blood into the microfluidic system.

12. The system of any preceding embodiment, the microfluidic chip further comprising: a membrane filter for blood separation coupled to the inlet channel and placed in the microfluidic network between the inlet and the wells.

13. The system of any preceding embodiment, the microfluidic chip further comprising: a buffer and reagent loading port connected to the inlet channel.

14. The system of any preceding embodiment, the imager comprising: a smartphone microscope imaging dark-field illumination of the chip based on evanescent fields within one or more wells generated by LED total internal reflections of the light source and fluorescence intensity.

15. The system of any preceding embodiment, the first light source comprising: a waveguide; and a plurality of light emitting diodes for wave guided excitation of nanoparticles by LED illumination.

16. The system of any preceding embodiment, the second light source comprising: a plurality of blue light emitting diodes for fluorescence detection of nucleic acids.

17. The system of any preceding embodiment, the microfluidic chip further comprising: a metal nanodisk within the first set of wells for enhancement of plasmonic light scattering to improve the limit of detection; and thin film photothermal heaters within the second set of wells for the nucleic acids amplification using photonic PCR.

18. A system for microfluidic sample analysis, the system comprising: (a) a detection assembly, the assembly comprising: (i) a housing with a slot opening configured to receive the microfluidic chip; (ii) a vacuum pump; (iii) a socket operably coupled to the vacuum pump, the socket configured to reversibly couple with at least one vacuum port of a microfluidic chip; (iv) a first light source directed to surfaces of a chip, the light source configured for excitation of nanoparticles by illumination; (v) a second light source directed to surfaces of a chip, the second light source configured for fluorescent excitation of nucleic acids; (vi) a heating element; (vii) a wireless receiver; (viii) a controller coupled to the vacuum pump, light sources, heating element, receiver and a power supply; and (b) a control and imaging interface assembly, the assembly comprising: (i) a display; (ii) a control interface configured to control functions of the detection assembly controller; (iii) a wireless transmitter; (iv) an imager; (v) a computer processor; and (vi) a non-transitory computer-readable memory storing instructions executable by the computer processor; (vii) wherein the instructions, when executed by the computer processor, perform steps comprising: (1) actuating the vacuum pump to draw fluid through a microfluidic chip coupled to the socket of the detection assembly; (2) activating the first light source configured for excitation of nanoparticles by illumination; (3) imaging the chip with the imager: (4) activating the second light source configured for fluorescent excitation of nucleic acids; (5) imaging the chip with the imager; and (6) analyzing the images.

19. The system of any preceding embodiment, wherein the instructions when executed by the computer processor further perform steps comprising: (a) activating heating elements to amplify nucleic acids and fluorescence; and (b) measuring fluorescence intensity of chip images.

20. The system of any preceding embodiment, wherein the instructions when executed by the computer processor further perform steps comprising: (a) transmitting images to a remote computer for analysis; (b) receiving analyzed data from the remote computer; and (c) displaying the received data on the display.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A system for microfluidic sample analysis, the system comprising:
   (a) a microfluidic chip body comprising:
      (i) a plurality of enclosed wells;
      (ii) a sample inlet that receives a fluid sample;
      (iii) a network of microfluidic channels coupled to the wells with at least one inlet channel that transports a fluid sample from the sample inlet to one or more wells; and
      (iv) at least one vacuum port connected to the network of microfluidic channels, said vacuum port configured to be coupled to a vacuum source to draw fluid through the network of microfluidic channels and wells;
   (b) a detection assembly, the assembly comprising:
      (i) a housing with a slot opening configured to receive the microfluidic chip;
      (ii) a vacuum pump;

(iii) a socket operably coupled to the vacuum pump, the socket configured to reversibly couple with at least one vacuum port of the microfluidic chip;
(iv) one or more light sources directed to surfaces of the chip, said light sources configured for excitation of nanoparticles by illumination;
(v) a controller coupled to the vacuum pump, light sources and a power supply; and
(vi) an imager.

2. The system of claim 1, wherein said inlet of said microfluidic chip further comprises:
a plurality of hollow micro-needles coupled to said channel;
wherein a user places a fingertip on the plurality of hollow micro-needles, such that the one or more hollow micro-needles penetrates an epidermal layer of skin to sample blood from capillary vessels underneath; and
wherein the vacuum pump generates a negative pressure within the inlet channel to withdraw a volume of blood into the microfluidic system.

3. The system of claim 1, said microfluidic chip further comprising:
a membrane filter for blood separation coupled to the inlet channel and placed in the microfluidic network between the inlet and the wells.

4. The system of claim 1, said microfluidic chip further comprising:
a buffer and reagent loading port connected to said inlet channel.

5. The system of claim 1, said wells of said microfluidic chip further comprising:
a metal nanodisk within the wells for enhancement of plasmonic light scattering to improve the limit of detection.

6. The system of claim 1, said light source further comprising:
a waveguide; and
a plurality of light emitting diodes for wave guided excitation of nanoparticles by LED illumination.

7. The system of claim 1, said imager comprising:
a smartphone microscope imaging dark-field illumination of the chip based on evanescent fields within one or more wells generated by LED total internal reflections of the light source.

8. The system of claim 1, said microfluidic chip further comprising:
a second set of wells connected to the network of microfluidic channels; and
microheating elements in proximity to the wells, said elements controlled by the controller.

9. The system of claim 8, said detection assembly further comprising:
a second light source configured for fluorescent excitation of nucleic acids.

10. A system for microfluidic sample analysis, the system comprising:
(a) a microfluidic chip body comprising:
(i) a first and second set of a plurality of enclosed wells;
(ii) a sample inlet that receives a fluid sample;
(iii) a network of microfluidic channels coupled to the sets of wells with at least one inlet channel that transports a fluid sample from the sample inlet to the sets of wells; and
(iv) at least one vacuum port connected to the network of microfluidic channels, said vacuum port configured to be coupled to a vacuum source to draw fluid through the network of microfluidic channels and wells;
(b) a detection assembly, the assembly comprising:
(i) a housing with a slot opening configured to receive the microfluidic chip;
(ii) a vacuum pump;
(iii) a socket operably coupled to the vacuum pump, the socket configured to reversibly couple with at least one vacuum port of the microfluidic chip;
(iv) a first light source directed to surfaces of the chip, said light source configured for excitation of nanoparticles or fluorescent particles by illumination;
(v) a second light source directed to surfaces of the chip, said second light source configured for fluorescent excitation of nucleic acids;
(vi) a heating element;
(vii) a controller coupled to the vacuum pump, light sources, heating element and a power supply; and
(viii) an imager.

11. The system of claim 10, wherein said inlet of said microfluidic chip further comprises:
a plurality of hollow micro-needles coupled to said channel;
wherein a user places a fingertip on the plurality of hollow micro-needles, such that the one or more hollow micro-needles penetrates an epidermal layer of skin to sample blood from capillary vessels underneath; and
wherein the vacuum pump generates a negative pressure within the inlet channel to withdraw a volume of blood into the microfluidic system.

12. The system of claim 10, said microfluidic chip further comprising:
a membrane filter for blood separation coupled to the inlet channel and placed in the microfluidic network between the inlet and the wells.

13. The system of claim 10, said microfluidic chip further comprising:
a buffer and reagent loading port connected to said inlet channel.

14. The system of claim 10, said imager comprising:
a smartphone microscope imaging dark-field illumination of the chip based on evanescent fields within one or more wells generated by LED total internal reflections of the light source and fluorescence intensity.

15. The system of claim 10, said first light source comprising:
a waveguide; and
a plurality of light emitting diodes for wave guided excitation of nanoparticles by LED illumination.

16. The system of claim 10, said second light source comprising:
a plurality of blue light emitting diodes for fluorescence detection of nucleic acids.

17. The system of claim 10, said microfluidic chip further comprising:
a metal nanodisk within the first set of wells for enhancement of plasmonic light scattering to improve the limit of detection; and
thin film photothermal heaters within the second set of wells for the nucleic acids amplification using photonic PCR.

18. A system for microfluidic sample analysis, the system comprising:
(a) a detection assembly, the assembly comprising:
(i) a housing with a slot opening configured to receive the microfluidic chip;

(ii) a vacuum pump;
(iii) a socket operably coupled to the vacuum pump, the socket configured to reversibly couple with at least one vacuum port of a microfluidic chip;
(iv) a first light source directed to surfaces of a chip, said light source configured for excitation of nanoparticles by illumination;
(v) a second light source directed to surfaces of a chip, said second light source configured for fluorescent excitation of nucleic acids;
(vi) a heating element;
(vii) a wireless receiver;
(viii) a controller coupled to the vacuum pump, light sources, heating element, receiver and a power supply; and (b) a control and imaging interface assembly, the assembly comprising:
(i) a display;
(ii) a control interface configured to control functions of the detection assembly controller;
(iii) a wireless transmitter;
(iv) an imager;
(v) a computer processor; and
(vi) a non-transitory computer-readable memory storing instructions executable by the computer processor;
(vii) wherein said instructions, when executed by the computer processor, perform steps comprising:
(1) actuating the vacuum pump to draw fluid through a microfluidic chip coupled to the socket of the detection assembly;
(2) activating the first light source configured for excitation of nanoparticles by illumination;
(3) imaging the chip with the imager;
(4) activating the second light source configured for fluorescent excitation of nucleic acids;
(5) imaging the chip with the imager; and
(6) analyzing the images.

19. The system of claim 18, wherein said instructions when executed by the computer processor further perform steps comprising:
(a) activating heating elements to amplify nucleic acids and fluorescence; and
(b) measuring fluorescence intensity of chip images.

20. The system of claim 18, wherein said instructions when executed by the computer processor further perform steps comprising:
(a) transmitting images to a remote computer for analysis;
(b) receiving analyzed data from the remote computer; and
(c) displaying the received data on the display.

* * * * *